United States Patent [19]

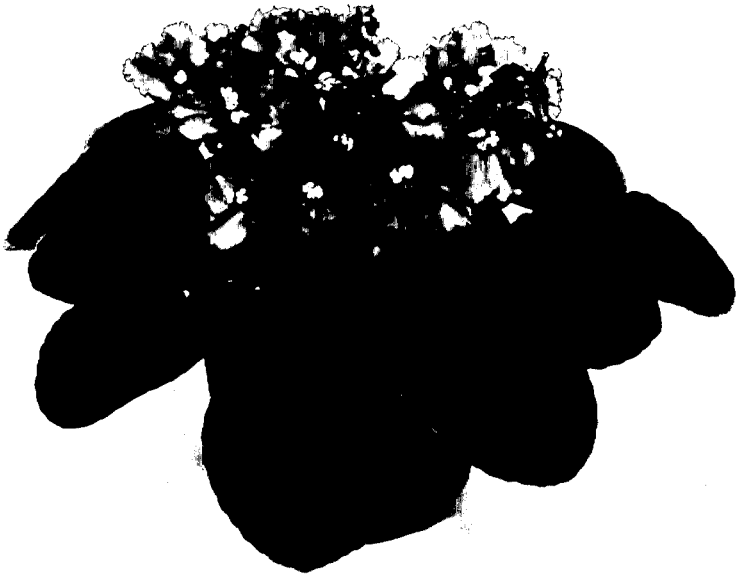

Fischer

[11] Patent Number: Plant 5,806

[45] Date of Patent: Nov. 18, 1986

[54] AFRICAN VIOLET PLANT NAMED ROMEO

[75] Inventor: Arnold Fischer, Hanover, Fed. Rep. of Germany

[73] Assignee: Ball Pan Am Plant Company, Parrish, Fla.

[21] Appl. No.: 632,109

[22] Filed: Jul. 18, 1984

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African Violet named Romeo, particularly characterized by its large dark violet flowers which are semi-double in form with slightly ruffled petal margins, upright peduncles, compact habit, profuse flowering, and by its medium green, pubescent foliage.

1 Drawing Figure

1

The present invention comprises a new and distinct cultivar of African Violet plant, botanically known as *Saintpaulia ionantha,* and hereinafter referred to by the cultivar name Romeo.

The new cultivar was referred to during the breeding and selection process by the designated V7-B53-V, and is a product of a breeding program. The basic objective of the breeding program was to create a new African Violet cultivar having profuse semi-double deep violet blooms held on erect peduncles above medium green foliage. The new cultivar was originated from a cross made in a controlled breeding program in Hannover, Germany. The male and female parents are unknown at this time.

Romeo was discovered and selected by me as a flowering plant within the progeny of the stated cross in a controlled environment in Fallbrook, Calif. Asexual reproduction of the new cultivar by leaf cuttings, as performed by me at West Chicago, Ill. and Parrish, Fla. has demonstrated that the combination of characteristics as herein disclosed for the new cultivar are firmly fixed and retained through successive generations of asexual reproduction.

Romeo has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Romeo which in combination distinguish this African Violet as a new and distinct cultivar:

(1) Large dark violet flowers.

(2) Flowers are semi-double with a slightly ruffled petal margin.

(3) Compact rosette habit with flowers borne on upright peduncles.

(4) Suitable for production in 10 cm. pots, flowering in 9–11 weeks depending upon growing conditions.

(5) Very floriferous, with flowers continuing to develop for weeks after onset of flowering.

(6) Medium green, pubescent foliage with a crenate leaf margin.

2

The new cultivar is most similar to Helga, disclosed in U.S. Plant Pat. No. 3,848. Romeo is principally distinguished from Helga by its semi-double flowers.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 5000 foot candles of natural light at approximately 2:30 P.M. in Parrish, Fla.

Botanical Classification: *Saintpaulia ionantha,* Ramat. cv. Romeo.

Parentage:

*Male parent.*—Unknown.

*Female parent.*—Unknown.

Propagation: The new cultivar holds its distinguishing characteristics through successive propagations by leaf cuttings.

Plant: From 6 cm. to 8 cm. tall when grown in pots, and approximately 24 cm. in diameter when fully grown. The growth rate is vigorous, and the general shape of the full grown plant is round.

*Leaves.*—Quantity: Abundant. Shape: Cordate with crenate margins. Diameter: 50–75 mm. Texture: Pubescent, glossy. Ribs and Veins: Pinnate. Color (upperside): 147A. Color (underside): 186A to 186D. Peticles: 2–8 cm. in length.

*Flowers.*—Buds: Size: Up to 1 cm. in diameter. Shape: Round. Rate of opening: Normal. Color: Dark violet, ranging from 79B to 80C. Sepals: Shape Lanceolate. Color: 183D with a hint of 147D. Phyllaries: 2, lanceolate. Color (upperside): 147A. Color (underside): 187A. Calyx: Shape: Funnel. Size: About 13 mm. in diameter. Aspect: Hairy.

*Peduncle.*—Length: 3–7 cm. Character: Rigid, erect. Color: 183A with a tint of 147D.

*Individual flowers.*—Number of petals: 5–10. Size: 35–40 mm. in diameter and 15 mm. deep. Shape: Cup when flower first opens and becomes flat as flower matures. Color: Upperside: 77A, and slightly darker in center; there is also a showing of 77B. Underside: 77D. Romeo shows slight variation in color due to light, temeperature and other growing conditions. Borne: Cymosa clusters formed on upright peduncles 3–7 cm. long. Flowering habit: Flowers profusely and intermittently year round with blooms lasting 2–3 weeks after which petals dry up but do not drop. A 2¼" plantlet placed in a 10 cm. pot finishes in 9–11 weeks.

*Reproductive organs.*—Stamens: 2, borne singly on one side of the ovary. Anthers basifixed. Anthers: 2 mm.×2 mm., yellow. Filaments: 3 mm., violet-yellow. Pollen color: Yellow. Pistels: Number: 1 3–6 mm. long. Styles: 1. Sitgma: Sticky, white. Ovaries: Superior.

*Roots.*—Fiberous and fine.

*Disease resistance.*—No African Violet diseases observed to date.

*General observations.*—Romeo is principally characterized by its many large flowers held aloft on erect peduncles above medium, green pubescent foliage. The plant habit is excellent, and the semi-double zygomorphic rotate flowers are dark violet in color.

I claim:

1. A new and distinct cultivar of African Violet named Romeo, as illustrated and described, and particularly characterized by its large dark violet flowers which are semi-double in form with slightly ruffled petal margins, upright peduncles, compact habit, profuse flowering, and by its medium green, pubescent foliage.

* * * * *